United States Patent [19]

Jackman et al.

[11] Patent Number: 6,025,514
[45] Date of Patent: Feb. 15, 2000

[54] PROCESS FOR PREPARING METHYL DITHIOCARBAZINATE BY REACTING METHYL BROMIDE WITH THE REACTION PRODUCT OF CARBON DISULFIDE, HYDRAZINE AND AN ADJUNCT BASE

[75] Inventors: Dennis E. Jackman, Prairie Village, Kans.; David T. Erdman, Kansas City, Mo.; Peter E. Newallis, Leawood, Kans.; Daniel M. Wasleski, Blue Springs, Mo.; Vijay C. Desai, Shawnee, Kans.; Jeffrey D. Macke, Kansas City, Mo.; Vidyanatha A. Prasad, Leawood, Kans.

[73] Assignee: Bayer Corporation, Pittsburgh, Pa.

[21] Appl. No.: 09/157,483

[22] Filed: Sep. 21, 1998

Related U.S. Application Data

[63] Continuation-in-part of application No. 08/962,130, Oct. 31, 1997, abandoned, which is a continuation of application No. 08/743,763, Nov. 7, 1996, abandoned.

[51] Int. Cl.$^7$ .................................................. C07C 333/28
[52] U.S. Cl. ............................................................. 558/233
[58] Field of Search ............................................. 558/233

[56] References Cited

U.S. PATENT DOCUMENTS

| | | | |
|---|---|---|---|
| 3,284,482 | 11/1966 | D'Amico et al. | 260/455 |
| 3,395,234 | 7/1968 | Hopkins et al. | 558/233 X |
| 4,696,938 | 9/1987 | Le | 514/343 |
| 5,466,854 | 11/1995 | Choi et al. | 558/233 |
| 5,861,526 | 1/1999 | Mayes | 558/233 |
| 5,877,339 | 3/1999 | Wasleski et al. | 558/233 |

FOREIGN PATENT DOCUMENTS

| | | |
|---|---|---|
| 3709414 | 2/1988 | Germany . |
| 1274521 | 5/1972 | United Kingdom . |

OTHER PUBLICATIONS

Audrieth et al., J. Organic Chem., vol. 19, pp. 733–471 (month unavailable) 1954.

S. Losanitch., J. Chem. Soc. vol. 119, pp. 763–765 (month unavailable) 1921.

Sandstrom et al, Arkiv för Kemi, vol. 4, No. 19 (month unavailable) 1952 297.

*Primary Examiner*—Michael G. Ambrose
*Attorney, Agent, or Firm*—Joseph C. Gil; Carol Marmo

[57] ABSTRACT

Disclosed herein is a process for preparing high yields of methyl dithiocarbazinate by reacting carbon disulfide, hydrazine and a base in an aqueous medium, in an effective ratio to form a dithiocarbazinate salt followed by methylating the dithiocarbazinate salt with methyl bromide.

5 Claims, No Drawings

PROCESS FOR PREPARING METHYL DITHIOCARBAZINATE BY REACTING METHYL BROMIDE WITH THE REACTION PRODUCT OF CARBON DISULFIDE, HYDRAZINE AND AN ADJUNCT BASE

CROSS-REFERENCE TO RELATED APPLICATIONS

This application is a Continuation-In-Part of U.S. application Ser. No. 08/962,130, filed Oct. 31, 1997, now abandoned, which in turn was a continuation application of U.S. application Ser. No. 08/743,763, filed Nov. 7, 1996, now abandoned.

BACKGROUND OF THE INVENTION

The present invention relates to an improved process for preparing methyl dithiocarbazinate. More specifically, the present invention relates to an improved process for preparing methyl dithiocarbazinate by reacting carbon disulfide, hydrazine and an adjunct base.

Illustrative of the prior art of preparing methyl dithiocarbazinate are the following: Audrieth et al., J. Organic Chem., Vol. 19, pp. 733–741 (1954) discloses a process for preparing methyl dithiocarbazinate and converting it to thiocarbohydrazide. The process comprises a dropwise addition of 1.04 moles of carbon disulfide to 1.18 moles of potassium hydroxide and 1.1 moles of 85% hydrazine in 200 ml. of ethanol, in an ice bath. A heavy yellow oil containing potassium dithiocarbazinate separates during the addition. The resulting mixture is stirred, chilled and two volumes of ether are added to cause separation of more of the desired product (potassium dithiocarbazinate).

The oily layer is separated from the ether-alcohol layer and filtered to remove a small amount of an unidentified solid which is formed. The clear yellow solution is then dissolved in 300 ml. of water. The resulting solution is cooled in an ice bath and 1.05 moles of methyl iodide is added in approximately 10 batches. The reaction vessel is shaken and cooled alternately after each such addition until the methyl iodide is consumed. The reaction mixture is allowed to stand for several hours, and shaken occasionally to permit complete reaction. The methyl dithiocarbazinate is collected and recrystallized from ethanol.

Methyl dithiocarbazinate (24.4 g, 0.2 mole) was dissolved in 200 ml. of absolute ethanol and 18 ml. (0.3 mole of hydrazine) of 85% hydrazine hydrate was added. The resulting solution was refluxed until no more solid thiocarbohydrazide precipitated (about 45 minutes). To remove a small amount of formed 3-hydrazino-4-amino-5-mercapto-1,2,4-triazole, the reaction mixture was chilled, and the resulting solid product was collected and recrystallized from acidified water (with a few drops of hydrochloric acid).

Le, U.S. Pat. No. 4,696,938 discloses a process for preparing and using methyl hydrazinecarbodithioate as an intermediate in the preparation of 6-aryl-pyridine thiosemicarbazones. Methyl dithiocarbazinate is prepared as follows: Hydrazine hydrate (150 g) is added to a cooled (0°C.) solution of potassium hydroxide in water (240 ml.) and 2-propanol(200 ml.). Pre-cooled carbon disulfide (182 ml.) is then added dropwise to the stirred reaction mixture, while maintaining the internal temperature below 10° C. After the addition is complete, stirring is continued for a further one hour. Cooled methyl iodide (426 g) is added dropwise for 1½ hour. The resulting white precipitate is collected via filtration and washed with cooled water. The crude product is recrystallized from methylene chloride.

To form 6-aryl-pyridine thiosemicarbazone, methyl dithiocarbazinate is reacted in a suitable solvent such as alcohol with the product of 6-aryl-2-alkylpyridine treated with selenium dioxide in a suitable ethereal solvent such as tetrahydrofuran or 1,4-dioxane.

S. Losanitch, J. Chem. Soc., Vol.119, pp. 763–765 (1921) discloses a process for preparing methyl dithiocarbazinate by first obtaining ammonium dithiocarbazinate and reacting it with methyl iodide. The ammonium dithiocarbazinate is obtained when a solution of hydrazine hydrate in alcohol, containing a large excess of ammonia, is slowly treated with cooling with the corresponding quantity of carbon disulfide. The methyl dithiocarbazinate is formed by treating the ammonium salt in a dilute alcohol solution with methyl iodide.

Sandstrom et al, Arkiv For Kemi, 4(1952) 297, discloses a process for preparing ethyl dithiocarbazinate by decomposing diethyltrithiocarbonate with hydrazine. The process involves the separation of hydrazinium dithiocarbazinate from an ethanol-water mixture and the reaction of the hydrazinium dithiocarbazinate with ethyl bromide in an ethanol-water mixture.

U.S. Pat. No. 3,284,482 discloses a process for preparing chlorobenzyl esters of dithiocarbazinic acid as follows: To a solution comprising 85% hydrazine, 25% sodium hydroxide and 300 ml. of water is added carbon disulfide, dropwise at 10 to 15° C. over 20 minutes. External cooling is removed and the reaction mixture is stirred for an hour at 25 to 30° C. Then, trichlorobenzyl chloride is added in one portion to the reaction mixture which is stirred for 24 hours at 25 to 30° C. to produce the corresponding trichlorobenzyl dithiocarbazinate. The product is then extracted with ethyl ether. The ether solution is washed with water until it becomes neutral, is dried over sodium sulfate, and the ether is removed in vacuo.

British Patent Specification 1,274,521 discloses dithiocarbazinic ester derivatives by reacting dithiocarbazinic acid esters with an oxo compound. The dithiocarbazinic acid is prepared by reacting hydrazine hydrate with carbon disulfide in alcohol medium in the presence of potassium hydroxide, ammonia or excess hydrazine hydrate.

After isolation, the dithiocarbazinic acid salt is converted into an ester by an alkylating or aralkylating step. This step is carried out in water, a mixture of water and alcohol or in alcohol. Alternately, the ester can be prepared by a method wherein the reaction is carried out in a single reactor. The alkylating or aralkylating agent is added to the dithiocarbazinic acid salt solution prepared by the above method. The alkylating or aralkylating agents disclosed by the patent are: dimethyl sulfate, diethyl sulfate, allyl chloride, n-butyl iodide, n-octyl ester, n-dodecyl bromide, cetyl bromide, benzyl chloride, p-chlorobenzyl chloride, p-isopropylbenzyl bromide, p-n-butylbenzyl bromide, and alphamethylbenzyl chloride.

As would be realized from the foregoing, there is a need for an economical process, i.e., a more facile and cost efficient process, for preparing methyl dithiocarbazinate. In particular, there is a need for a more economic commercial process for preparing methyl dithiocarbazinate. By the present invention, there is provided such an improved process for preparing methyl dithiocarbazinate.

SUMMARY OF THE INVENTION

Surprisingly, it has been found that methyl dithiocarbazinate can be prepared by a facile and cost effective process. This improved process comprises reacting hydrazine, carbon disulfide and a base in an aqueous reaction medium, in an effective ratio to form a dithiocarbazinate salt, followed by reacting (methylating) the dithiocarbazinate salt with methyl bromide. The aqueous reaction medium is selected from the group consisting of water and a mixture of water and a non-alcoholic hydrocarbon solvent.

In the present embodiment of the invention, carbon disulfide, hydrazine, and an inorganic base are reacted in an aqueous medium as the reaction vehicle. The resulting reaction mixture comprising dithiocarbazinate salt is reacted with methyl bromide to produce high yields of methyl dithiocarbazinate. Preferably, the aqueous reaction medium is water.

In contrast, the prior art processes generally involved the reaction of carbon disulfide and hydrazine in a reaction medium containing alcohols; separation of the resulting dithiocarbazinate; the use of relatively more expensive or more intractable and sometimes commercially cost prohibitive alkylating agents such as methyl iodide; and catalysts such as sodium iodide and/or recrystallization of the resulting methyl dithiocarbazinate.

It is a distinct feature of the invention that by using the process of the invention one can eliminate the use of undesirable methylating agents such as methyl iodide, undesirable solvents such as alcohols, and expensive catalysts such as sodium iodide. It is a distinct feature of the invention that the process requires short reaction times, requires no isolation of intermediate dithiocarbazinate salts, and no recrystallization of the final methyl dithiocarbazinate. Consonantly, the process of the invention fills a long felt but unmet need of using a facile process for preparing methyl dithiocarbazinate by using readily available and relatively less expensive reactants and solvents, and processing techniques.

In the practice of the invention, methyl dithiocarbazinate can be used as an intermediate compound in the preparation of other chemicals such as thiadiazoles.

DETAILED DESCRIPTION OF THE INVENTION

More particularly, the present invention is directed to a process for preparing methyl dithiocarbazinate comprising:

a) reacting carbon disulfide, hydrazine and an adjunct base in an aqueous reaction medium to form a dithiocarbazinate salt, wherein
   i) said base is added in such a manner that the pH of the reaction mixture is maintained between about 8 and about 14,
   ii) the molar ratio of carbon disulfide to hydrazine to base falls in the range of (1 to 1.2):(1 to 1.2):(1 to 1.2), and
   iii) said aqueous reaction medium is selected from the group consisting of water and a mixture of water and a non-alcoholic hydrocarbon solvent, and
b) methylating said salt with methyl bromide.

The invention relates broadly to a process for preparing methyl dithiocarbazinate (MDTC) by: (I) reacting carbon disulfide with hydrazine and a base in an aqueous reaction medium and in an effective ratio to form a dithiocarbazinate salt followed by (II) methylating the dithiocarbazinate salt of (I) with methyl bromide. The process can be represented by reactions (I) and (II), as follows:

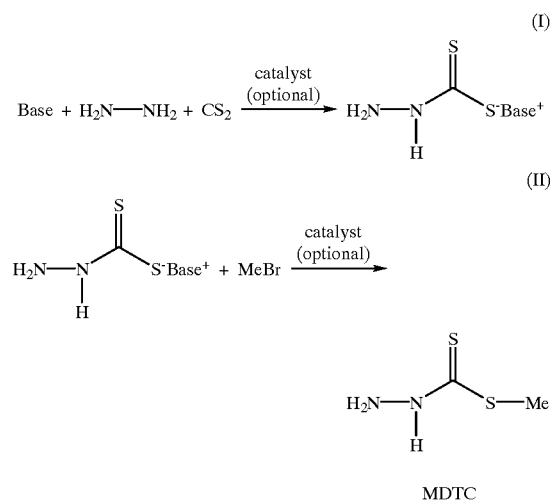

MDTC

Carbon disulfide, hydrazine (usually in the form of hydrazine hydrate), and an inorganic base are reacted in amounts such that the mole ratio falls in the range of (1 to 1.2):(1 to 1.2):(1 to 1.2) and, preferably, 1:1:1. For example, carbon disulfide and the inorganic base may be added to hydrazine simultaneously and, preferably, dropwise. Alternately, the inorganic or organic base can be first charged to the hydrazine, and then the carbon disulfide may be added, preferably dropwise. In either case, a phase transfer catalyst can be used.

The reaction must be conducted in a pH range that does not adversely affect the reaction. Typically, the reaction can be conducted in a pH range of from about 8 to about 14 and preferably from about 9 to about 14. The pH can be controlled by the slow addition of an appropriate base. In general, when relatively weak bases (such as ammonium hydroxide or amines) are used, no special cautions have to be taken. When stronger bases (such as sodium hydroxide) are used, the base should be added at such a rate to maintain the pH within the above-noted range. The reaction temperature can be about 0 to 35° C. and preferably 5 to 25° C. Time of the reaction can be about 1 to 4 hours and preferably from 1 to 2 hours.

As the base, one can employ inorganic and nitrogenous bases as described hereunder. The base, in contradistinction with hydrazine, is described herein as an adjunct base. The inorganic base is preferably sodium hydroxide. It is believed without being bound to any particular theory that, other than sodium hydroxide, other inorganic bases that can affect sufficient ion exchange with the hydrazinium ion can be used. Illustrative of these other inorganic bases would be potassium hydroxide and lithium hydroxide. As the nitrogenous base, one can employ a nitrogenous compound such as ammonia, ammonium hydroxide and various organic mono-and diamines. Some amines which can be used include ethanolamine, di-n-propylamine, diisopropylamine, di-n-butylamine, t-butylamine, dimethyl benzylamine, ethylmethyl pyridine, and menthanediamine.

The aqueous reaction medium is preferably water and may contain a non-alcoholic hydrocarbon solvent. The mole ratio of water to carbon disulfide can be from about 2:1 to about 10:1 and preferably from about 2:1 to about 5:1. Useful non-alcoholic hydrocarbon solvents include aromatic solvents such as xylene, cumene, benzene, toluene, ethyl benzene and mesitylene, and aliphatic solvents such as pentane, hexane, cyclohexane and heptane. If used, the preferred solvent is an aromatic solvent which is preferably toluene. When a solvent is used, the solvent to carbon disulfide molar ratio is from about 0.1:1 to about 3:1 and is preferably from about 0.15:1 to about 2:1. Unlike many of the prior art processes, the reaction medium of this process does not contain alcoholic solvents. The aqueous reaction medium of the present process is selected from the group consisting essentially of water, and a mixture of water and a non-alcoholic hydrocarbon solvent.

The resulting product comprising the dithiocarbazinate salt is reacted with methyl bromide. The mole ratio of methyl bromide to the dithiocarbazinate salt can be from 1.5 to 1.02:1, and is preferably 1.05:1. The methylation reaction temperature can be from about 0 to 35° C., over a period of about 0.5 to 3 hours and preferably 1 to 2 hours. The water, and optionally the solvent, and the catalyst employed in reaction (II) are essentially the same as described in reaction (I). The mole ratio of the water to the dithiocarbazinate salt is from about 2:1 to about 10:1 and preferably from about 2:1 to about 5:1. If solvent is used, the mole ratio of the solvent to the dithiocarbazinate salt can be from about 1.3:1 to about 0.17:1 and is preferably 0.5:1. If used, the catalyst can be used in amounts of about 0.5 mole % to 10% preferably 0.5% to 1% per mole of dithiocarbazinate salt.

While the methylation reaction (II) can be conducted in another vessel, it is typically conducted in the same reaction vessel as used in the preparation of the dithiocarbazinate salt. It is a distinct feature of the invention that the methylation reaction can be conducted without isolating the dithiocarbazinate salts of reaction (I). In this embodiment of the invention, the methylation reaction (II) consists essentially of reacting the reaction product of reaction (I) with methyl bromide.

It is also a distinct feature of the invention that the methylation reaction (II) can be conducted without the use of expensive reaction catalysts such as sodium iodide. In this regard, the methylation step consists essentially of reacting the reaction product of (I) with methyl bromide.

The resulting product containing methyl dithiocarbazinate can be isolated by any convenient means such as filtering or centrifuging. The methyl dithiocarbazinate can be collected on a vacuum filter and washed with water to remove impurities such as potassium bromide salt. The resulting wet cake can be used as such or dried by any means that is effective to provide the requisite drying without causing its decomposition. Illustratively, the product can be dried at temperatures that do not cause decomposition of the products. More specifically, the product can be dried in a vacuum oven, using a nitrogen sparge at a temperature of about 30° C. to 40° C. Generally, the methyl dithiocarbazinate purity can be up to about 95 percent with variation attributable to washing and/or drying steps. As would be realized from the above, methyl dithiocarbazinate can be obtained without recrystallization of the reaction product of reaction (II). Therefore, methyl dithiocarbazinate can be prepared by a process consisting essentially of reacting carbon disulfide, hydrazine and a base in an aqueous reaction medium, in an effective ratio to form a dithiocarbazinate salt, followed by the methylation of the dithiocarbazinate salt with methyl bromide, and removing the bromide salt.

A catalyst, such as a phase-transfer catalyst can be employed in the reaction(s). An example of the catalyst is tris-[2-(2-methylethoxy) ethyl] amine(TDA-1), N-benzyltrimethylammonium hydroxide, N-methylimidazole, dimethylaminopyridine, 1,4-diazabicyclo-(2,2,2)-octane and diethylene glycol. The mole ratio of the catalyst can be 0 to 100 mmoles and preferably 0 to 1 mmoles per mole of carbon disulfide.

As can be seen from the foregoing, the process of the invention is well suited to commercial applications because it employs readily available reagents and processing techniques. Illustratively, the process can be carried out under reaction conditions which do not produce environmentally unacceptable by-products, reduce yield, affect quality of the end products or adversely impact production operations.

These and other aspects of the invention are further illustrated but are not intended to be limited by the following examples in which all parts and percentages are by weight unless otherwise specified.

EXAMPLES

Example 1

Preparation of Methyl Dithiocarbazinate (MDTC) using Aqueous KOH as Base

In a properly equipped reaction vessel, carbon disulfide (19 g, 0.25 mole) was slowly added (with cooling) to a mixture of toluene (43.25 g, 0.46 moles), water (72 g, 4 moles), TDA-1 (2.02 g, 0.0063 moles), and hydrazine monohydrate (50 g, 1.0 mole) at <25° C. When the pH of the resulting slurry stabilized at pH 9, aqueous potassium hydroxide (43%, 32.6 g., 0.25 mole) was added and the solution was stirred until the pH dropped to 9. Three more equal portions of carbon disulfide (19 g, 0.25 moles) and potassium hydroxide (43%, 32.6 g, 0.25 moles) were added using the same protocol. After the completion of the addition of these portions, the reaction mixture was stirred for 90 minutes.

Methyl bromide gas (104.4 g, 1.1 moles) was bubbled into the yellow mixture over one hour. The resulting white slurry was stirred for an additional 30 minutes at 25° C., cooled to 5° C. and filtered. Methyl dithiocarbazinate was isolated as a white powder at 77% yield. The major impurities were water and potassium bromide.

Example 2

Preparation of Methyl Dithiocarbazinate (MDTC) using Aqueous NaOH

Hydrazine hydrate (101 g, 2 moles) and water (70 ml) were added to a 1 liter, 4-neck round bottom flask. The mixture was cooled to 50° C. and carbon disulfide (153.8 g, 2 moles) were slowly added dropwise. When the pH had dropped to below 7.8, 50% sodium hydroxide (172 g, 2.15 moles) were added dropwise to maintain the pH at about 8.5. The mixture was stirred for about 1 hour after the carbon disulfide addition was complete. Methyl bromide (220 g, 2.3 moles) was added at 20° C. over four hours. The pH was maintained at about 8 by addition of 12 g of 50% sodium hydroxide. The mixture was cooled to 5° C. when the excess methyl bromide began to reflux and was then filtered. After washing with a small amount of cold water and toluene, 193 g of 97.5% MDTC were obtained. The net yield was 77.1%.

Example 3

Comparative—No pH Control 315 ml of water and 1 mole of 50% sodium hydroxide were added to a 1 liter, 4-neck round bottom flask. The mixture was cooled to 20° C. and 50 g of hydrazine hydrate were added. 1 mole of carbon disulfide was then added over 1 hour while maintaining the temperature at 20° C. One mole of methyl bromide was then added over 1 hour and the mixture was stirred for 30 minutes at room temperature. The mixture was then filtered, washed with water and then with ethyl acetate. A few grams of white solids with a melting point of about 164° C. were obtained. The composition of the solids was not MDTC.

Example 4
Preparation of Methyl Dithiocarbazinate (MDTC) using Ammonium Hydroxide In a properly equipped reaction vessel, hydrazine hydrate (75.0 g, 1.50 mol.) was slowly added (with cooling) to a mixture of ammonium hydroxide (87.1 g, 1.54 mol.) and water (75 g, 4.16 moles) at <5° C. Carbon disulfide (114.0 g, 1.50 mol.) was then added (1.0 hour) to the mixture while maintaining the temperature at 5° C. After the mixture had been stirred for about 1 hour at the same temperature, toluene (43.25 g, 0.46 moles) and diethylene glycol (4.47 g, 0.042 moles) were charged, and methyl bromide (156.7 g, 1.65 mol.) was introduced over a period of 2 hours at 5° C. The mixture was agitated for 1 hour at 25° C., cooled to 0 to 5° C., and the solids were filtered. The solids were washed with ice-cold water (3×25 ml.), and then dried (overnight at 40° C./20 mm) to yield 177.1 g (77.6%) of white crystals. The mother liquor contained an additional 3 to 5% net yield of MDTC. No specific steps were taken to maintain the pH because a relatively weak base (i.e., ammonium hydroxide) was used.

Example 5
Preparation of Methyl Dithiocarbazinate (MDTC) using t-Butylamine

In a properly equipped reaction vessel, hydrazine hydrate (75.0 g, 1.50 mol.) was slowly added (with cooling) to a mixture of t-butylamine (109.7 g, 1.50 mol.) and water (75 g, 4.2 moles) and toluene (43.25 g, 0.469 moles) at <5° C. Carbon disulfide (114.0 g, 1.50 mol.) then was added (1 hour) to the mixture while maintaining the temperature at 5° C. After the mixture had stirred for about 1 hour at the same temperature, methyl bromide (156.7 g, 1.65 mol.) was introduced over a period of 2 hours at 5° C. The mixture was agitated for 1 hour at 25° C., cooled to 0 to 5° C., and the solids were filtered. The solids were washed with ice-cold water (3×25 ml.), and then dried (overnight at 40° C./20 mm) to yield 156.4 g, (81.0%) of white crystals. The mother liquor contained an additional 3 to 5% net yield of MDTC. No specific steps were taken to maintain the pH because a relatively weak base (i.e., t-butylamine) was used.

Example 6
Preparation of Methyl Dithiocarbazinate (MDTC) using KOH

In a properly equipped reaction vessel (four neck, 1000 ml.) hydrazine hydrate (50.0 g,1.0 mol.) was slowly added (with cooling) to a mixture of toluene (86.5 g, 0.94 moles), water (72 g, 4.0 moles) and TDA-1(2.0 g, 0.00062 moles) at <25° C. Carbon disulfide (12.7 g, 0.167 mol.) was added dropwise over a 10 minute period while maintaining the temperature at 25° C., followed by the addition of KOH (21.75 g, 0.167 mol) over a 10 minute period, while maintaining the temperature at 25° C. The incremental addition of carbon disulfide and KOH was repeated five times. This incremental addition kept the pH from getting very high. Methyl bromide (104.5 g, 1.1 moles) was then added over a period of 2 hours at 25° C. The reaction mixture was cooled to 0 to 5° C., and filtered under vacuum. The resultant product was then washed with cold water and then dried in a vacuum oven (40° C./20 mm) to yield 92.8 g (76.1%) of MDTC. The mother liquor contained an additional 3 to 5% net yield of MDTC.

Examples 7 and 8
Comparative—Using Process of British Patent 1,274,521

Example 7
Omitting use of Ethanol

Hydrazine hydrate (50 g, 1 mole), water (87 g) and potassium hydroxide (1.05 moles) were added to a 1 liter, 4-neck round bottom flask. The mixture was cooled to 5° C. and carbon disulfide (80 g, 1.05 moles) then added dropwise with stirring. Stirring was continued for an additional hour. Dimethyl sulfate (132 g, 1.05 moles) and water (250 ml) were simultaneously added dropwise over 30 minutes. The mixture was stirred for 1 hour, and filtered to yield 13.8 g of MDTC and some yellow oil. Stirring the oil and the aqueous mother liquor with 100 ml of toluene gave another 7.2 g of MDTC. The total yield was 17.2%.

Example 8
Use of Comparable Amount Water in Place of Ethanol

Hydrazine hydrate (50 g, 1 mole), water (137 g) and potassium hydroxide (1.05 moles) were added to a 1 liter, 4-neck round bottom flask. The mixture was cooled to 5° C. and carbon disulfide (80 g, 1.05 moles) then added dropwise with stirring. Stirring was continued for an additional hour. Dimethyl sulfate (132 g, 1.05 moles) and water (250 ml) were simultaneously added dropwise over 30 minutes. The mixture was stirred for 1 hour, and filtered to yield 6.0 g of MDTC and some yellow oil. Stirring the oil and the aqueous mother liquor with 100 ml of toluene gave another 8.7 g of MDTC. The total yield was 12.0%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing methyl dithiocarbazinate comprising:
    a) reacting carbon disulfide, hydrazine and an adjunct base in an aqueous reaction medium to form a dithiocarbazinate salt, wherein
        i) said base is added in such a manner that the pH of the reaction mixture is maintained between about 8 and about 14,
        ii) the mole ratio of carbon disulfide to hydrazine to base falls in the range of (1 to 1.2):(1 to 1.2):(1 to 1.2), and
        iii) said aqueous reaction medium is selected from the group consisting of water and a mixture of water and a non-alcoholic hydrocarbon solvent, and
    b) methylating said salt with methyl bromide.

2. The process of claim 1 wherein the adjunct base is sodium hydroxide.

3. The process of claim 1 wherein the adjunct base is a nitrogenous base selected from the group consisting of ammonia, ammonium hydroxide and an amine.

4. The process according to claim 1 wherein the reaction is conducted in the presence of a catalyst.

5. The process of claim 1, wherein the mole ratio is 1:1:1.

* * * * *